US012603148B2

(12) United States Patent (10) Patent No.: US 12,603,148 B2
Franke et al. (45) Date of Patent: Apr. 14, 2026

(54) METHOD FOR ANALYSIS OF OMICS DATA

(71) Applicant: Max-Delbrück-Centrum für Molekulare Medizin in der Helmholtz-Gemeinschaft, Berlin (DE)

(72) Inventors: Vedran Franke, Berlin (DE); Bora Uyar, Berlin (DE); Jonathan Ronen, Berlin (DE); Altuna Akalin, Berlin (DE)

(73) Assignee: MAX-DELBRUCK-CENTRUM FUR MOLEKULARE MEDIZIN DER HELMHOLTZ-GEMEINSCHAFT, Berlin (DE)

( * ) Notice: Subject to any disclaimer, the term of this patent is extended or adjusted under 35 U.S.C. 154(b) by 307 days.

(21) Appl. No.: 18/274,271

(22) PCT Filed: Jan. 19, 2022

(86) PCT No.: PCT/EP2022/051118
§ 371 (c)(1),
(2) Date: Jul. 26, 2023

(87) PCT Pub. No.: WO2022/161824
PCT Pub. Date: Aug. 4, 2022

(65) Prior Publication Data
US 2024/0087677 A1 Mar. 14, 2024

(30) Foreign Application Priority Data
Jan. 29, 2021 (EP) ..................................... 21154353

(51) Int. Cl.
G16B 20/00 (2019.01)
G16B 40/20 (2019.01)
G16H 70/60 (2018.01)

(52) U.S. Cl.
CPC ............. *G16B 20/00* (2019.02); *G16B 40/20* (2019.02); *G16H 70/60* (2018.01)

(58) Field of Classification Search
CPC ......... G16B 20/00; G16B 40/20; G16H 70/60
See application file for complete search history.

(56) References Cited

U.S. PATENT DOCUMENTS

2018/0314795 A1* 11/2018 Cheung ................. G06F 40/169
2020/0286587 A1 9/2020 Israeli et al.
(Continued)

OTHER PUBLICATIONS

Ronen, Evaluation of colorectal cancer subtypes and cell lines using deep learning, 2019, Life Sci Alliance, 2(6):e201900517 (Year: 2019).*
(Continued)

*Primary Examiner* — Kambiz Abdi
*Assistant Examiner* — Tran N Nguyen
(74) *Attorney, Agent, or Firm* — RENNER, OTTO, BOISSELLE & SKLAR, LLP

(57) ABSTRACT

A method for analysis of omics data related to samples derived from a human, animal or disease model is disclosed. The method comprises the steps of: a) Determining a plurality of latent spaces by inputting the omics data into a plurality of omics neural networks in parallel and achieving a plurality of latent spaces each comprising a set of latent factors by performing the calculations of the plurality of omics neural networks in a data processing unit, wherein the output of the omics neural networks each provides a respective latent space; b) Consolidating the plurality of latent spaces into one reproducible latent space, wherein the step of consolidating is processed by a data processing unit; wherein the consolidated latent factors represent characteristics of the samples to be analyzed.

15 Claims, 5 Drawing Sheets

(56)                    References Cited

U.S. PATENT DOCUMENTS

| | | | |
|---|---|---|---|
| 2021/0150663 A1* | 5/2021 | Maiyuran | G06T 1/60 |
| 2021/0375395 A1* | 12/2021 | Rabizadeh | G16B 5/00 |
| 2023/0028666 A1* | 1/2023 | Ray | G06T 1/60 |
| 2023/0215091 A1* | 7/2023 | Drabinski | G06T 15/005 |
| | | | 345/426 |

OTHER PUBLICATIONS

International Search Report from corresponding International Patent Application No. PCT/EP22/51118, dated Apr. 14, 2022.
Ronen, et al., "Evaluation of colorectal cancer subtypes and cell lines using deep learning." Life science alliance 2.6 (2019).
Uyar, et al. "Multi-omics and deep learning provide a multifaceted view of cancer." bioRxiv (2021).
Jurmeister, et al., "Machine learning analysis of DNA methylation profiles distinguishes primary lung squamous cell carcinomas from head and neck metastases", Sci Transl Med., Sep. 11, 2019, vol. 11; eaaw8513.
Chalise, et al., "Integrative clustering methods for high-dimensional molecular data", Transl Cancer Res., Jan. 1, 2014, pp. 202-216.
European Search Report from corresponding European Patent Application No. 21154353.3, dated Jul. 5, 2021.

* cited by examiner

|      | $LF_1$ | $LF_2$ | $LF_3$ | $LF_4$ | $LF_5$ | $LF_6$ | $LF_7$ | $LF_8$ |
|------|--------|--------|--------|--------|--------|--------|--------|--------|
| $OD_1$ | $P_{11}$ | $P_{12}$ | $P_{13}$ | $P_{14}$ | $P_{15}$ | $P_{16}$ | $P_{17}$ | $P_{18}$ |
| $OD_2$ | $P_{21}$ | $P_{22}$ | $P_{23}$ | $P_{24}$ | $P_{25}$ | $P_{26}$ | $P_{27}$ | $P_{28}$ |
| $OD_3$ | $P_{31}$ | $P_{32}$ | $P_{33}$ | $P_{34}$ | $P_{35}$ | $P_{36}$ | $P_{37}$ | $P_{38}$ |
| $OD_4$ | $P_{41}$ | $P_{42}$ | $P_{43}$ | $P_{44}$ | $P_{45}$ | $P_{46}$ | $P_{47}$ | $P_{48}$ |
| $OD_5$ | $P_{51}$ | $P_{52}$ | $P_{53}$ | $P_{54}$ | $P_{55}$ | $P_{56}$ | $P_{57}$ | $P_{58}$ |
| $OD_6$ | $P_{61}$ | $P_{62}$ | $P_{63}$ | $P_{64}$ | $P_{65}$ | $P_{66}$ | $P_{67}$ | $P_{68}$ |

Fig. 4

METHOD FOR ANALYSIS OF OMICS DATA

FIELD OF THE INVENTION

The invention relates to a method for analysis of omics data related to samples derived from a human, an animal or a disease model.

The method further relates to a computer program, computer-readable storage medium and data processing apparatus arranged for carrying out the steps of this method.

BACKGROUND OF THE INVENTION

There is a need for analysis of omics data related to samples derived from humans, animals or disease models, for example to analyse a biopsy of a patient in order to determine characteristics of the samples, which allows, in particular, diagnosis and prognosis of diseases and drug responses. The determination of the characteristics of the samples allows, for example, to detect tumorigenic processes, to predict drug response, to predict the probabilities of survival of a patient, and to find similar patients within at least one cohort.

J. Ronen, S. Hayat, A. Akalin: "Evaluation of Colorectal Cancer Subtypes and Cell-Lines Using Deep Learning", Feb. 12, 2019, GOI: 10.26508/LLSA.201900517 discloses a multi-omics autoencoder integration method that incorporates data on gene expression, copy number variation and somatic mutations in identifying colorectal cancer subtypes. A deep learning-based method allows to measure the similarity between colorectal tumors and disease models such as cancer cell-lines by learning latent factors representing the patterns that are clinically relevant and explain the variability of molecular profiles across tumors and cell-lines.

The latent factors are extracted by use of a multimodal, stacked variational auto-encoder. The architecture and depth of the neural network makes it non-trivial to associate the input genomic features (gene expression, mutations, etc.) with the different latent factors.

SUMMARY OF THE INVENTION

The present invention improves on the known methods for analysis of omics data related to samples derived from a human, an animal or a disease model.

In order to analyse omics data related to samples derived from a human, an animal or a disease model, the method comprises steps of:
- a) determining a plurality of latent spaces by inputting the omics data into a plurality of omics neural networks in parallel and achieving a plurality of latent spaces each comprising a set of latent factors by performing the calculations of the plurality of omics neural networks in a data processing unit wherein the output of the omics neural networks each provides a respective latent space;
- b) consolidating the plurality of latent spaces into one reproducible latent space, wherein the step of consolidating is processed by a data processing unit;

wherein the consolidated latent factors represent characteristics of the samples to be analysed.

The method is based on the use of the plurality of omics neural networks rather than one omics neural network in the prior art. A plurality of latent spaces is provided, each latent space comprising a set of latent factors. The set of latent spaces determined in parallel by the plurality of omics neural networks are then consolidated into one reproducible latent space. This has the effect of a reproducible latent space with improved quality of the resulting latent factors which represent characteristics of the samples to be analysed.

Composite biomarkers are measured for the sample as a result of the consolidated latent factors, including gene expressions, represent the biomarkers. Thus, the method for analysis of omics data related to samples is a method for measuring biomarkers for a sample by analyzing the omics data and achieving consolidated latent factors representing characteristics of the sample to be analysed as biomarkers.

The omics data stored in a data memory are read out and forwarded to at least one data processing unit, wherein a computer program performs calculations of at least one omics neural network and is performed with the processor by use of the omics data to calculate and (permanently or intermediately) store a latent factor data set, i.e. a respective latent space, in a data memory. The stored latent factor data provided by the plurality of omics neural networks are forwarded to a data processing unit, wherein a computer program performs calculations arranged for consolidating the latent factor data of the plurality of latent spaces into a set of consolidated latent factor data providing one reproducible latent space. The data processing unit used for processing the omics neural networks and the data processing unit for consolidating the latent spaces can be either the same unit or different units from each other. The set of consolidated latent factor data representing characteristics of the samples are stored in a data memory. They can be read out by a data processing unit for further processing in order to analyse the samples in more detail, e.g. to detect disease processes, to predict drug responses, to predict patient survival probabilities, to find similar patients and the like.

The sample can be a biopsy, e.g. a tissue, of a human or an animal. Such sample can be collected by a doctor from a patient, for example, to obtain a primary tumor sample. The method can also be performed on samples derived from disease models such as cancer cell lines, patient derived xenografts (PDX), organoids, or model organisms.

The samples can be processed to determine e.g. DNA- and/or RNA-sequence data to obtain data from multiple omics platforms, i.e. to obtain data using two or more kinds of omics data e.g. by profiling multiple types of molecular features through sequencing (multi-omics data). Thus, multiple omics data modalities can be achieved.

The omics data related to the sample are used as input value for an omics neural network which provides latent factors as its output. The group of latent factors of an omics neural network is a latent space describing characteristics of the sample.

An omics feature represents a molecular cellular constituent (a molecular unit) amenable to quantification by one or more omics assays. Omics feature can be a DNA sequence of one or more nucleobases, from one or more genomic locations; relative or absolute amount of a particular DNA sequence; the chemical modification status of a DNA sequence (for example, DNA methylation); relative or absolute amount of an RNA sequence corresponding to a particular gene or transcript; the chemical modification status of the RNA molecule; relative or absolute amount of a particular protein sequence; chemical modification status of the protein sequence; relative or absolute amount of a cellular metabolite.

Omics data are composed of one or more omics features quantified by one or more assays (experimental procedures) in multiple samples.

Omics data can be selected from different types of omics data. The omics data can be related to at least one quantitative or qualitative, direct or indirect, measurement of molecular constituents of a cell or of a group of cells, related to samples derived from human, animal or disease models. For example, omics data can be related to at least one of the following omics data type matrices: gene expression, number of gene copies, alterations of gene copies, mutation, methylation, proteomics, phosphorproteomics, metabolomics, microbiomics, chromatin accessibility measurement, DNA localization of proteins, DNA localization of histone posttranslational modifycations, RNA modifications, DNA modifications, transcriptional rates, RNA stability, transcript expression, splicing quantification, gene fusions, DNA structural variation, RNA structural measurements, translational rates and differential polyadenylation.

The omics data can be derived from different gene sequencing assays of tissue samples or cell cultures. They can also be derived by use of computer processed simulations of gene feature data.

According to the present invention, a plurality of latent spaces is provided by a plurality of omics neural networks using the same omics data as input value. The repeated determination of latent spaces by use of a plurality of omics neural networks improve the reproducibility of the result when consolidating the plurality of latent spaces to achieve consolidated latent factors representing characteristics of the samples to be analysed.

The obtained plurality of latent spaces can be used for predicting at least one covariate as the output of a predictor.

Using the generated latent space in this way has the advantage of a reduced batch effect and improves the prediction of labels. The at least one covariate at the output of the predictor comprises, most preferably, at least one of the characteristics of the sample to be analysed.

The at least one covariate can comprise at least one of the characteristics selected from the group of quantitative or qualitative phenotypic measurements, quantitative or qualitative cellular measurements, quantitative or compositional tissue or organ measurements, patient data, historical patient data, or data related to sample processing.

The covariates can be selected from covariates of different types. The characteristics of the samples to be analysed can be selected from the covariates, including but not limited to, undesired batch effects, survival outcome endpoints (e.g. overall/progression free/disease free survival), drug response, undesired separation between model classes, age, gender, tumor stage, relevant exposure histories, tumor micro-environment composition, T-cell exhaustion, B-cell exhaustion, immunomodulatory score, imaging derived features, tumor cell replication rate, tumor microbiome composition, probability of metastasis, histological types/subtypes, tumor subtype classification, pathway activity scores, gene essentiality score, signalling pathway activation, propensity of differentiation and sternness score.

The above is further achieved by the method for training the plurality of omics neural networks which are provided for the above method for the analysis of omics data.

The training of the plurality of omics neural networks comprises the steps of:

determining a plurality of latent spaces by inputting omics data into a plurality of omics neural networks in parallel and achieving a plurality of latent spaces, each comprising a set of latent factors by performing the calculation of the plurality of omics neural networks in a data processing unit, wherein the output of the omics neural networks each provides a respective latent space;

predicting at least one covariate as the output of the classifier by use of the obtained plurality of latent spaces; and training of the plurality of omics neural networks by use of the error between the predicted at least one covariate and a respective known covariate related to the omics data, wherein the plurality of omics neural networks are trained to improve the posterior probability distribution of the latent spaces produced by the plurality of omics neural networks and to predict a set of predefined desired covariates by feedback of the at least one error between the predicted at least one covariate and a respective known covariate related to samples derived from a human, an animal or a disease model.

The training of the plurality of omics neural networks by inputting the omics data does not result in the same set of weighting factors in the employed omics neural networks. Instead, a variation of the plurality of omics neural networks occurs. This has the effect of an increased reproducibility of the latent spaces which latent factors represent characteristics of the samples to be analysed.

Preferably different Artificial Intelligence (AI) models are trained on different omics data. Thus the plurality of omics neural networks can be trained independently from each other with different sets of omics data and related known covariates.

For example, omics data related to disease samples and healthy controls (e.g. cancer data) comes from different sequencing assays. Said omics data can include sets of gene copy number and gene expression and/or mutation. Samples representing patients and/or disease models (e.g. tumor models) including, for example, cell lines, organoids etc. can be collected and evaluated. Sometimes, samples are a part of a larger study, which is a natural grouping of samples. Cohorts of patients can be formed, wherein results in studies, may be mixed and matched across the studies. A cohort report is about a cohort of patients (cases), and is associated with a specific model, i.e., an assigned omics neural network. A plurality of reports can be assigned to one common omics neural network.

This provides different sets of omics data related to a set of covariates, wherein said different sets of omics data are used to train the plurality of omics neural networks differently from each other. This results in a variation of AI models, which are later used in parallel for one set of omics data related to a sample for analysing this sample.

Preferably, omics features included in the set of omics data are determined which affect a selected latent factor used as a biomarker.

A matrix of the products of the absolute values of weights of at least one of the omics neural networks can be determined to represent the neural path product for the interaction of each omics feature included in the set of omics data and each latent factor. Omics features having a value of the neural path product in the matrix of products above a threshold are determined as omics features which affect the latent factor. The threshold can define a floating threshold for the value of the neural path product coming with ordering the neural path products in the matrix of products by value (i.e. by importance) and taking a predefined number N of the top values, i.e. a percentile threshold. The threshold could also be a fixed threshold for the value of the neural path product, i.e. a cutoff. The cutoff can preferably be considered in a second step after consideration of the floating threshold by ranking the values of the neural path product in a respective column or line in the matrix.

The absolute neural path product can be represented by a matrix of the products of the absolute values of weights of a related omics neural network arranged with the types of omics data in the columns and the types of latent factors in the row. Those products of the absolute values of weights above the threshold value are used to select the related relationship of omics type and related latent factor. This provides a reliable and easy analysis of the relationship between specific types of omics data and latent factors.

Preferably, the plurality of omics neural networks each comprises a stacked variational encoder to extract latent factors and a decoder to extract omics data from the latent factors provided at the output of the related stacked variational encoder. The use of such a multi-omics auto-encoder had been found a reliable tool for determining latent factors from omics data.

The latent factors in the latent spaces can be determined by a plurality of omics neural networks comprising a defined number (N) of selected latent factors and/or latent factors determined to be related to a characteristic of interest of the analysed sample.

The step b) of consolidating the plurality of latent spaces determined by the plurality of omics neural networks comprises, in an improved embodiment of the present invention, the steps of selecting latent factors which are similarly present in a minimum number of the plurality of latent spaces, and the step of clustering the selected latent factors. Thus, only latent factors which appear in at least a number of M latent spaces within a defined range of similarity are kept and stored in a data memory for further processing. Also latent factors which are kept and stored are then divided into groups (clustered), wherein each cluster contains latent factors from at least a number P (where P is less than or equal to M) of latent spaces. All these latent factors in a cluster are within a predefined range of similarity of each other, so that it can be considered as the same latent factor. Each cluster of latent factors can be averaged and produce a single consolidated latent factor which represents a characteristic of the sample.

Preferably, the step b) of consolidating the plurality of latent spaces determined by the plurality of omics neural networks comprising the steps of:

Comparing each latent factor of each of the latent spaces with each latent factor from each of the other latent spaces and selecting the latent factors which are present in at least a defined number N (N=integer number) of latent spaces within a given similarity range; Similarity can be for example, an Euclidean distance, cosine similarity, or any distance measure.

Calculating a respective average of the selected latent factors in a cluster for each of the clusters wherein the resulting average is a single latent factor related to a respective cluster, and wherein the set of single latent factors for the plurality of clusters form a consolidated latent space of the plurality of omics neural networks.

The latent factors can be compared to investigate if they appear in another run with defined similarity.

The average can be calculated for example as mean value, median value or the like.

In more detail, the step b) of consolidating the plurality of latent spaces determined by the plurality of omics neural-networks can be carried out by:

comparing each latent factor in each of the latent spaces with each latent factor from each of the other latent spaces using a similarity or distance metric, wherein a latent factor from a latent space is said to be present in another latent space if the similarity metric is above a defined threshold or the distance metric below a defined threshold, for some latent factor in that other latent space;

grouping (clustering) of latent factors which are present in at least a defined number N of the latent spaces together into clusters such that each cluster contains those latent factors from many latent spaces which are similar to each other according to said similarity or distance metric and thresholds; and calculating a respective average of the selected latent factors in each cluster for each of the clusters, wherein the resulting average is a new single latent factor related to a respective cluster of latent factors; and combining the latent factors from each of the averaged clusters into a new consolidated latent space of the plurality of omics neural networks.

The consolidated latent factors are related to at least one of the characteristics of the samples of humans, animals or disease models, which samples are related to the omics data. The consolidated latent factors can be related to the covariates which represent medical, biochemical or chemical characteristics of a sample.

Preferably, the consolidated latent factors of interest, which contain information about the characteristics of the sample are selected from the group of undesired batch effects, patient survival probability, drug response, undesired separation between model classes, tumor stage, relevant exposure histories, tumor microenvironment composition, T cell exhaustion, B cell exhaustion, immunomodulatory score, imaging derived features, tumor cell replication rate, tumor microbiome environment composition, probability of metastasis, tumor subtype classification, pathway activity scores, gene essentiality score, signaling pathway activation, propensity to differentiation and sternness score. The set of characteristics can be detected by use of the respective value of a related latent factor or consolidated latent factor obtained when inputting the omics data obtained from the sample into the plurality of omics neural networks.

The omics data can be extracted from at least one sample of a human, an animal or a disease model. For example, a biopsy can be processed with DNA and RNA extraction and sequencing in order to obtain omics data related to the biopsy, e.g. expression, copy-number, mutation annotation format file providing aggregated mutation information, and the like.

BRIEF DESCRIPTION OF THE DRAWINGS

The invention is explained in the following by way of example with the enclosed figures. It shows:

FIG. 4—Matrix of neural path products for pairs of omics data types and latent factor types to determine functional relationships;

DETAILED DESCRIPTION OF THE
INVENTION

Figure 1:
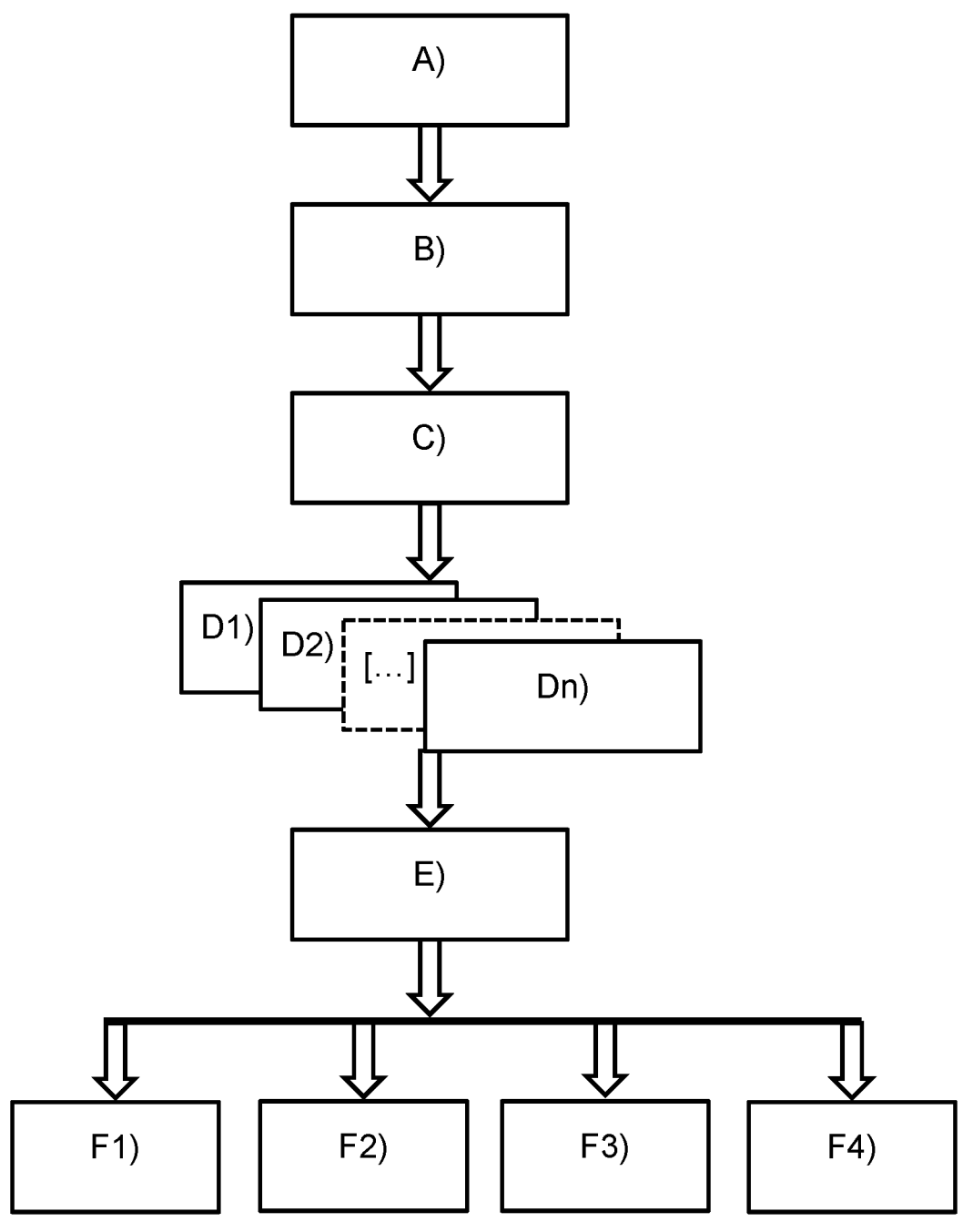
FIG. 1—Flow diagram of the method for analysis of omics data.

FIG. 1 shows a flow diagram of the method for analysis of omics data.

In a preferred embodiment, disease-related patient samples and/or related tissue samples or cell culture samples are mapped to a so-called "latent space" learned from existing data. The latent space is latent data provided as the output of the trained omics neural networks, which represent characteristics of the patient and the related sample.

In a step A), samples are collected from patients or animal disease models. For example, biopsies from tumors, which had been taken from a patient, are used for further processing.

In a step B), the samples are technically inspected, for example, by use of standard procedures of DNA and RNA extraction and sequencing.

In a step C), the sequenced DNA and RNA data is quality checked and quantified. This can include the quantification of the gene expression levels or detection of mutations from sequenced DNA. The result is a set of omics data related to the sample.

In the following steps D) to F), the sample is mapped to a latent space, i.e. the sample is analysed to determine characteristics of the sample.

In step D1), D2), D3), [ . . . ], Dn), with n as integer number, a plurality of latent spaces is determined by inputting the omics data into a plurality of omics neural networks in parallel and achieving a plurality of latent spaces each comprising a set of latent factors by performing the calculations of the plurality of omics neural networks in a data processing unit, wherein the output of the omics neural networks each provides a respective latent space The omics data that are read out of a data memory and forwarded into a data processing unit for processing omics neural networks includes, but are not limited to:

expression, which can be a text table data type;
copy-number, which can be a text table data type with per gene copy number
mutation data in a MAF file, which can be a text file containing coordinates, ensemble gene identifiers, mutation type, genomic context which bases change to what, sample identification, donor identification, etc.

A batch effect correction can be applied to the omics data using existing methods. The batch effect correction can be part of the neural network training procedure when the latent space is learned, i.e. constructed.

In step E), the plurality of latent spaces, each comprising a set of latent factors as output of a respective omics neural network, are consolidated into a reproducible latent space, wherein the consolidated latent factors represent characteristics of the sample to be analysed. The step of consolidating is processed by a data processing unit when running a computer program with executable program code on the data processing unit. The consolidated latent factors are stored in a data memory for further processing.

In step F1), F2), F3), [ . . . ], Fm), with m as integer number, the stored consolidated latent factors forming a consolidated latent space related to the sample are further processed. One or more of these optional steps Fm) can be selected and processed.

For example, step F1) is provided to detect disease processes, e.g. tumorigenic processes. The consolidated latent space for the analysed sample and stored similar consolidated latent spaces related to other patients can be used to find underlying disease (e.g. cancer) processes driving the cell.

Step F2), can be, for example, used to predict drug response. The consolidated latent space has information of drug response for some samples. This information can be essentially used to predict drug response for individual patients.

For example, step F3) provides a method to predict the survival probability of a patient. The consolidated latent space has information on genes and mutations that are important for survival. This information can be used to predict the survival probability and remaining lifetime probability on patients.

Step F4), for example, can be used to find similar patients. Mapping the patients to the consolidated latent space related to the sample of the patient provides the option of finding relationships with other patients having similar sets of latent factors. Similarities in groups of latent factors represent, for example, molecular similarity of the patients. The patients that are close to each other in the consolidated latent space have similar genes turned on/off, have similar mutations affecting similar pathways. This allows to predict the course of disease on most likely therapy from similar patients.

Preferably, a feature selection of features that go into the latent space mapping can be performed, e.g. by selecting a number N of the most variable features and/or by selecting the features known a-priori to be important for a disease of interest in general (e.g. cancer in general) or a specific disease type. Genes which are included in panel sequencing can be considered, as well as gene sets which have been published in the scientific literature.

Figure 2:
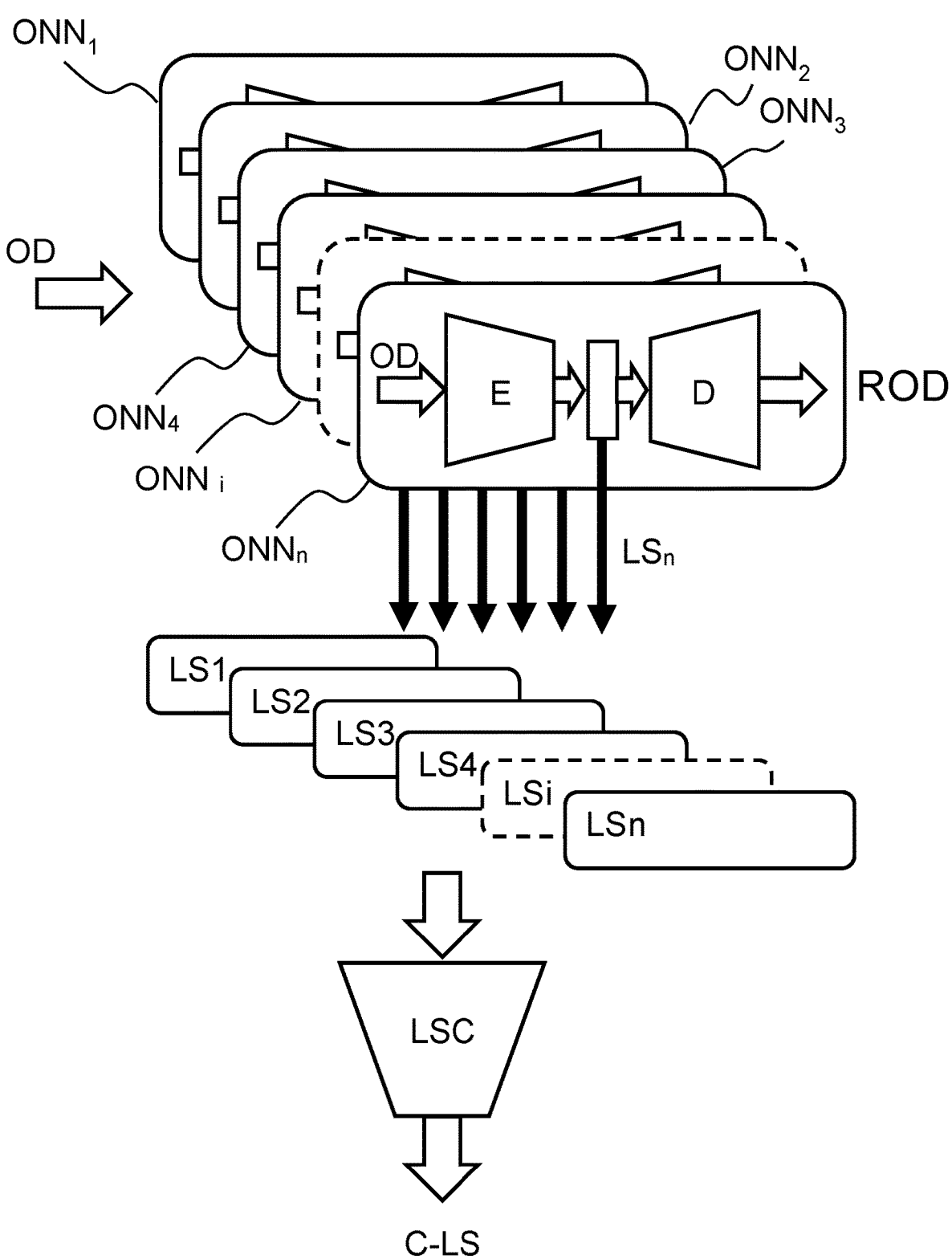
FIG. 2—Block diagram of a plurality of omics neural networks providing latent spaces and a subsequent consolidator.

FIG. 2 shows a block diagram of a plurality of omics neural networks providing latent spaces and a subsequent consolidator.

The omics neural networks can be provided by a computer program and database of trained weighting factors. Preferably, a stacked variational autoencoder is used for an omics neural network $ONN_i$, with i as integer number 1, 2, [ . . . ], n. The variational autoencoder comprises an encoder E including a neural network with an input layer using the omics data OD as input numbers and with an output layer providing a set of latent factors forming a latent space LS. The variational autoencoder further comprises a decoder D including a neural network with an input layer using the latent factors of the latent space LS provided as the output of the encoder E as input numbers and with an output layer providing a set of reconstructed omics data ROD at the output as output numbers.

The omics data OD are passed in the input of a respective omics neural network ONNi. Each omics neural network $ONN_1$, $ONN_2$, $ONN_3$, $ONN_4$, $ONN_5$, $ONN_n$ determines a respective set of latent factors, i.e. a respective latent space $LS_1$, $LS_2$, $LS_3$, $LS_4$, $LS_i$, $LS_n$.

The plurality of latent spaces $LS_1$, $LS_2$, $LS_3$, $LS_4$, $LS_i$, $LS_n$ processed and stored by the plurality of omics neural network $ONN_1$, $ONN_2$, $ONN_3$, $ONN_4$, $ONN_i$, $ONN_n$ are further processed by a latent space consolidator LSC to achieve a consolidated set of latent factors, i.e. one consolidated latent space C-LS.

The latent space can be constructed from existing datasets. For example, primary tumors from available datasets and/or disease models (e.g. patient derived xenografts, cell lines, organoids etc.) from available databases can be used (e.g. from "The Cancer Genome Atlas" (TCGA), the data portal of the "International Cancer Genome Consortium" (ICGC), the "Cancer Cell Line Encyclopedia" (CCLE) or the "Catalogue Of Somatic Mutations In Cancer" (COSMIC)).

The latent space can be constructed using the known Multi-omics Autoencoder Integration method, preferably with modifications.

In particular, the present invention makes use of an ensemble of autoencoders to improve the stability. This is shown in the block diagram of an omics neural network and subsequent predictor presented in FIG. 3.

In this preferred embodiment, a setup of encoder E, decoder D and a predictor CLA for each omics neural network ONNi is used only during training, which encourages the latent space LS to fulfil predefined requirements. These requirements can be selected from the group of results not including batch effects, results being predictive of survival and results being predictive of drug response.

The training of the omics neural network ONNi can happen according to the following criteria:

1. The encoder E is a neural network which predicts, for each patient in the cohort, the latent space LS representation. The encoder E is a variational encoder which makes the latent space representation be close, for samples with similar omics data. In a preferred embodiment, the encoder E is a variational encoder with a Gaussian prior.

2. The decoder D is a neural network which reconstructs the omics input data OD from the latent space LS representation. The reconstruction, i.e. the reconstructed omics data ROD, is to be as close as possible to the input, i.e. the omics data OD.

By training the encoder E and the decoder D in tandem, the latent space LS becomes a valuable compression of the omics data OD. The encoder E learns to produce latent space LS representations which the decoder D learns how to reconstruct the input from, guaranteeing that as much information from the input is present in the latent space LS.

The encoder and decoder D in the basic neural network architecture above has only the following criteria for constructing the latent space:

1. The latent factors are squeezed towards an a priori defined multivariable probability distribution, e.g. a Gaussian prior.

2. The latent factors enable the decoder to reconstruct the input omics data OD.

However, there are other criteria of interest to enforce on the latent space LS, for instance:

1. That the latent space LS does not reflect batch effects present in the input data;

2. That the latent space LS is predictive of patient survival;

3. That the latent space LS is predictive of drug response.

In order to do that, an encoder E, decoder D and predictor CLA framework is proposed, wherein 1. The encoder E is trained to produce latent space LS representations from input omics data OD;

2. The decoder D learns to reconstruct the omics data ROD from the latent space LS;

3. The predictor CLA learns to predict the covariate(s) of interest from the latent space, for example batch effects, survival, drug response, etc. The predictor is trained by use of true (known) label data TLD (i.e. data values representing covariates of interest) to predict label data PLD, which are compared with the true label data TLD to reduce the error between true and predicted label data PLD in the training process.

The training criteria are, for example:

1. The encoder E produces latent spaces LS with a gaussian prior (as above);

2. The decoder D reconstruction ROD should be as close as possible to the input data OD. Thus ensuring relevant information is kept in the latent space LS representation;

3. The predictor CLA should not be able to predict negative (undesirable) covariates (e.g. batch effect), thus ensuring that the encoder E produces latent spaces LS which are not reflective of batch effects;

4. The predictor CLA should be able to predict the positive (desirable) covariates (survival, drug response, etc.), thus ensuring that the encoder E produces latent spaces LS which are predictive of the desired properties.

When processing these trained omics neural networks $ONN_i$ by use of omics data OD related (e.g. measured) from a sample as input data the ensemble of omics neural networks $ONN_i$ improves the reproducibility of the characteristics of the sample obtained with the latent spaces LS.

Repeated runs of the basic model above result in latent spaces LS which are not 100% reproducible (technically, they tend to be rotations of each other). But the latent space LS is made up of so-called latent dimensions (latent factors), which are intended to be used as building blocks for biomarkers. Hence, it is important that these are reproducible.

A plurality of omics neural networks $ONN_i$ are trained, producing a plurality of latent spaces LS. For analysing a specific sample with the trained set of omics neural networks $ONN_i$, the latent spaces LS are processed with a latent space consolidator LSC, which produces a single consolidated latent space C-LS from the ensemble input. This is shown in FIG. 2.

Each latent factor (dimension) of each of the latent spaces LS can be compared with each latent factor from each of the other latent spaces LS by the consolidator LSC. Only latent factors which appear in at least N latent spaces (within some similarity threshold) are kept and stored. All the latent factors which are kept (stored) are divided into groups (clustered). Each cluster contains latent factors from at least N latent spaces LS. All the latent factors in a cluster are within some "sameness" threshold of each other, so that they can be considered as the same latent factor. Each cluster of latent factors can be averaged by the consolidator LSC to produce a single consolidated latent factor. The resulting latent factors are the dimensions of the consolidated latent space C-LS.

New samples can be mapped onto the latent space LS learned, as described above, by using the encoder neural networks and latent space consolidator LSC. The decoders D and/or predictors CLA used for training can be omitted for analysing samples with trained omics neural networks $ONN_i$.

In the following, an improved method for interpretation of the latent factors obtained with the analysis is explained.

The latent factors which make up a latent space LS have the potential to be valuable biomarkers. For example some of them are predictive of patient survival or resistance to certain therapies.

Each latent factor can be calculated from the omics data OD according to a formula:

$$z = \text{ReLu}(W_1 \text{ReLu}(W_2, \ldots, \text{ReLu}(W_N x), \ldots))$$

Where $z_i$ is the latent factor value, ReLu( . . . ) is a rectifier function, $W_i$ are weights of the neural encoder E network, and x is normalized omics data OD. Once a latent factor value $z_i$ has been deemed to be useful as a biomarker, it is necessary to explain which biological process it represents. This is done by examining the genes from the input omics data OD which affect the latent factor. This can be done using the absolute neural path product $P_{OL}$.

The absolute neural path product $P_{OL}$ is given by the sum of the weights within all paths between an omics data type O of interest and a latent factor type L of interest. This can be expressed with the formula:

$$P_{OL} = \Pi |W_i|,$$

Where the set of absolute neural path products $P_{OL}$ for all omics data types 0 and latent factors L of interest establish a matrix of n input omics data types (e.g. genes) and m latent factor types, with n and m as integer numbers.

FIG. 4 shows a matrix of absolute neural path products $P_{OL}$ for pairs of omics data types and latent factor types to determine functional relationships.

The omics data types in the matrix, which affect a latent factor L of interest with value $z_i$ are the omics data types with the highest values of the absolute neural path product $P_{OL}$ in the respective column of the matrix.

Thus, a threshold value for the absolute neural path product $P_{OL}$ can be given for the absolute neural path products $P_{OL}$ and all connections between the omics data types 0 and latent factor types L each linked by an absolute neural path product $P_{OL}$ above the given threshold value are considered to be functionally related.

A consolidated neural weight product can be calculated from a plurality of omics neural networks by averaging the neural weight products between a gene and latent factors originating from a plurality of omics neural networks. The consolidation of the neural weight product is performed based on the clustering of the plurality of latent factors.

A variety of clinical applications of the latent space are applicable.

For example, similar patients or disease models can be found. The consolidated latent space C-LS helps to identify which other patients and disease models are most similar to each other.

This can be done, for example, by some simple distance metric applied to each sample's consolidated latent space C-LS representation. Distance metrics which are relatively useless when applied to the high-dimensional input omics space can be used in the consolidated latent space C-LS due to its lower dimensionality, in particular the Euclidean distance, the cosine distance and the correlation distance.

Each sample can be compared to each other sample using these metrics, and the closest ones can be identified as being similar to each other.

This can also be done, for example, by clustering. Clustering methods (e.g. k-means, hierarchical clustering, etc.) are also applicable in high-dimensional omics space, but are more effective in the consolidated latent space C-LS. Samples in the latent space LS or more preferably in the consolidated latent space C-LS are clustered. Samples falling in the same cluster are identified as being similar.

The K-means clustering can be done by varying K and computing a benchmark for each value of K, e.g. Log-rank test for differential survival, GSEA (Gene Set Enrichment Analysis) for differential underlying biological processes, Silhouette scores for cluster cohesiveness, adjusted mutual information with some other labelling of the data (e.g. a-priori known cancer subtypes). For each value of K, some cluster may be identified which satisfies one of the benchmarks above. The samples in that cluster are identified as similar.

For the hierarchical clustering, a dendrogram is constructed based on distances in the consolidated latent space C-LS. The tree is cut at different heights, and at each height the same benchmarks as above are applied. Again, for each cut height, any cluster which satisfies some benchmark criterion, is deemed to contain similar samples.

Finding similarities can also be done by network diffusion.

The consolidated latent space C-LS representation of the samples is converted to a nearest-neighbour network. In that network, each sample is connected to another sample if it is one of its nearest neighbours. A diffusion process in the nearest neighbour network identifies the "distance-in-the-network" between each pair of samples. The distance in the network is used to determine which samples are similar to each other Finding similarities can also be done by classification.

This applies when identifying similar patients from different cohorts or sample types, e.g. identifying tumor models which are similar to primary tumors, or identifying tumors from cohort B which are similar to a subset of tumors from cohort A.

There exists a subset of samples in cohort A which is self-similar by some measure, e.g. they all respond to the same drug, they all share environmental factors (e.g. smokers), and/or they were deemed to make a group using one of the other methods above.

For identifying samples in cohort B, which are similar to this group in cohort A, a classifier on cohort A is trained, with the input being the latent space LS and the output being group membership. The classifier can be, for example, at least one classifier (predictor) selected from the group of: a feed-forward neural network, gradient boosted trees, random forest, and generalized linear model.

Then, the trained classifier is applied to cohort B, to find similar samples. For instance, cohort B might be primary tumors in a clinical trial, and cohort A a collection of tumor models. The subset in cohort A might be tumor models which are resistant to a drug.

Using a classifier allows to find similar patients in cohort B.

Another clinical application is the detection of disease processes, e.g. tumorigenic processes.

Once a set of similar samples has been identified, it is desired to identify any disease processes, e.g. oncogenic processes, that differentiate these patients from other groups.

This can be done by feature enrichment in omics space. A group is identified using the encoder-decoder network and the techniques mentioned above. The group is then analysed using standard feature enrichment techniques directly on its (and other groups') omics features, e.g. GSEA (Gene Set Enrichment Analysis), hypergeometric test, etc.

This can also be done by interpretation of latent factors. Once a set of similar samples has been identified, the latent factors which contribute to this grouping are identified. This can be done by using enrichment analysis on the latent space LS and/or training a classifier on the latent space LS to recognize this subset and examining the classifier weights (e.g. a Lasso, Cox regression, etc.).

Once the latent factors which contribute to this group's identification are identified, each latent factor is treated as a gene set, as explained for the interpretation of latent factors above. Then each of the consolidated latent factors C-LS can be associated with underlying biological processes, e.g. by GSEA (Gene Set Enrichment Analysis) against a library of pathways/gene sets. Preferably, this can be done by evaluating the absolute neural path product as explained above.

Another clinical application is the drug response prediction.

This can be done based on classifiers. Latent factors are used to construct computational drug prediction models based on in vitro cancer models (such as patient-derived xenografts (PDX), organoids or cell lines). These computational models are used for prediction of drug efficacy on samples of interest (patient samples). Classifiers contain inbuilt feature variable importance ranking (i.e. elastic net, random forest or a neural network), which are used to rank the underlying latent factors which contribute to prediction performance of each individual drug. The ranked latent factors are combined with the above described autoencoder feature importance extraction to find the most predictive biomarkers (gene expression panels and single nucleotide changes) which contribute to the differential drug performance.

This workflow enables prediction of drug efficiency, as well as being a biomarker discovery pipeline.

The drug response prediction can also be done based on network-diffusion. In addition, the latent spaces derived by the multi-omics autoencoder integration method can be combined with diffusion map based distances to approximate the distances on the data manifold. This enables local network based propagation of features (i.e. drug response) from samples on which a feature has been measured (i.e. PDX) onto samples of interest (patient samples). The distances are also combined with various weights that introduce prior knowledge about the relationships between the samples.

Another clinical application is the survival prediction. The latent factors can be used to predict patient survival, using off-the-shelf methods, e.g. Cox Regression or Random Survival Forests.

The use of the method for analysis of omics data related to samples derived from a human, animal or a disease model, i.e. to measure biomarkers for the sample, by obtaining a latent space and using of latent factors from that latent space for various technical purposes is explained by some examples. The biomarkers can be used e.g. to predict drug response, predict patient survival, find similar patients in a cohort, detect disease processes and the like.

Figure 3:
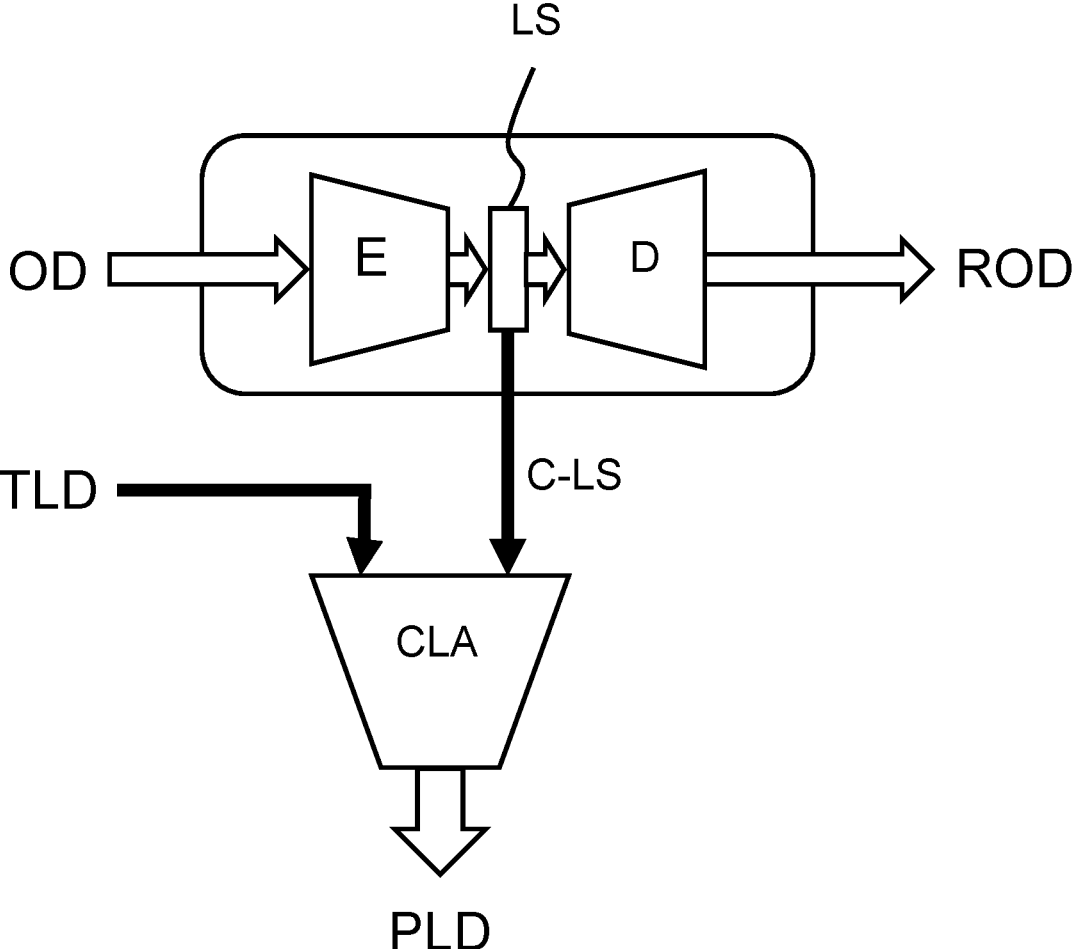
FIG. 3—Block diagram of an omics neural network and subsequent predictor.

This involves the use of the joint training of an encoder-decoder (autoencoder) and a classifier or regressor (henceforth, supervisor), as illustrated in FIG. 3.

The supervisor ("Classifier" in the figure above) may be a classifier or a regressor, depending on the nature of the "true label data in" (supervision signal). In the case of categorical labels, a classifier is used. In the case of a continuous signal, a regressor is used. For instance, in the first example below (Latent factors predict drug response), the supervision signal is a categorical (binary) label of response or non-response to a treatment, and hence a classifier is used. Meanwhile, in the second example ("Latent factors predict patient survival"), the supervision signal is the continuous signal of survival duration, and thus a regressor is used.

Following the joint training of the encoder-decoder-supervisor N times and obtaining N latent spaces, consolidation of those into a single latent space is performed as described above and in the claims.
A) Example Use Case: Latent Factors Predict Drug Response This method obtains latent factors from multi-omics data. The latent factors may be used in all the same ways that latent factors obtained using previous methods may be. An example of previous methods is described in reference [1]. The use of latent factors to predict drug response in primary tumors is demonstrated in reference [2], wherein FIG. 5 relates to immunotherapy and FIG. 6 to chemotherapy. The following is a demonstration of this use case using targeted therapies as well as chemotherapies in disease models.
Data Description:

A library of 37 patient derived xenografts (PDX) from localized breast cancer tumors were assayed using RNA-seq to determine gene expression profiles and Exome-seq to detect somatic mutations. AC (a combination of the chemotherapies Adriamycin (doxorubicin) and cyclophosphamide) was tested on the 37 PDXs, and 33 were also treated using Olaparib (a PARP inhibitor). The responses of the PDX to the treatments are categorized into Complete Response and non/incomplete response. 11 of the samples showed a complete response to AC (and 26 non- or partial responses), and 5 showed a complete response to Olaparib (and 28 non- or partial responses). Thus, the complete response to Olaparib results in 28 False and 5 True samples. The complete response to AC results in 26 False and 11 True samples.
Results:

The aforementioned data analysis pipeline was run on this data, producing a latent space consisting of a set of latent factors which were subsequently tested for association with the drug response variables (complete response to either Olaparib or AC).

The consolidated latent factors included the Latent Factor LF50 which could be clearly identified as biomarker which predicts response to Olaparib. The following table lists mean values and standard deviations for the LF50 values by response to Olaparib:

| Complete response to Olaparib | True | False |
|---|---|---|
| LF50 mean (std) | 16.89 (7.81) | 0.33 (1.31) |

Figure 5:
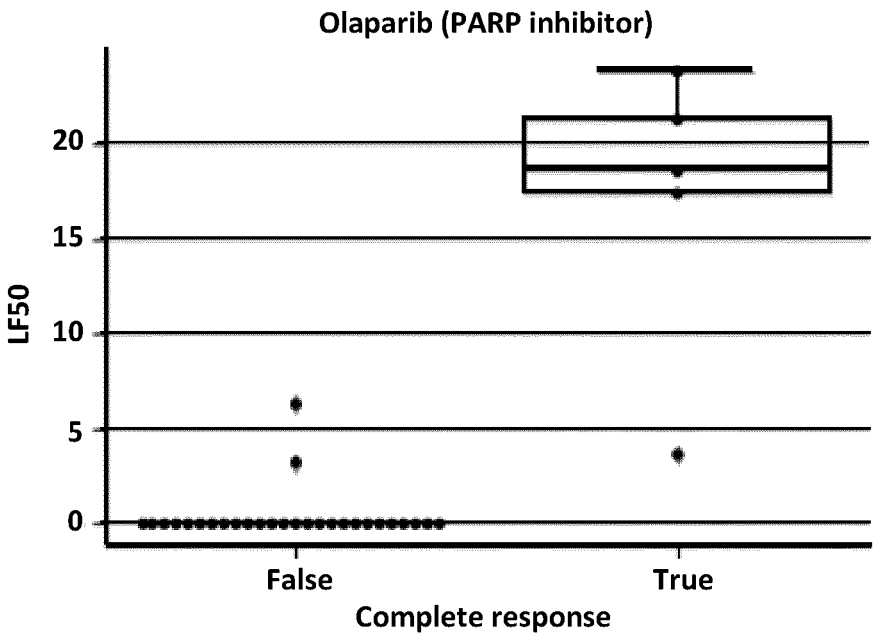
FIG. 5—Exemplary diagram of the complete response of latent factor LF50 as biomarker for Olapa rib (PARP-inhibitor)

This represents a statistically significant difference (two-sided t-test, P<0.00001). FIG. 5 illustrates the same graphically:

The consolidated latent factors included the latent factor LF1 as biomarker predicting response to AC. The following table lists mean values and standard deviations for LF1 values by response to
AC:

| Complete response to AC | True | False |
|---|---|---|
| LF1 mean (std) | 0.09 (0.31) | 1.86 (2.84) |

Figure 6:
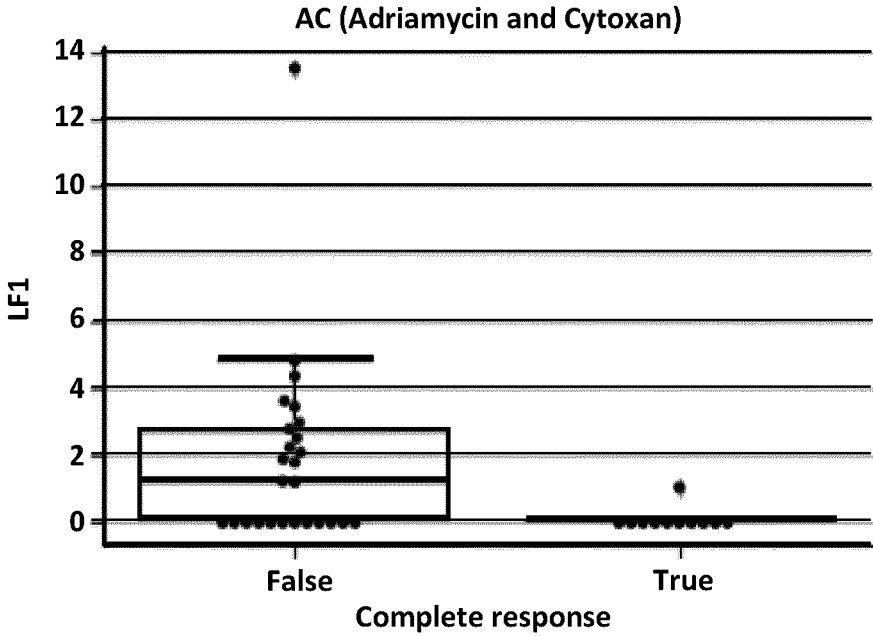
FIG. 6—Exemplary diagram of the complete response of latent factor LF1 as biomarker for AC (Adriamycin and Cytoxan).

This represents a statistically significant difference (two-site t-test, P<0.05). FIG. 6 illustrates the same graphically:

Thus, it is shown that the invention, whereby the latent space is obtained by the use of the drug response supervision signal, as well as the omics reconstruction signal (the cited methods use only the reconstruction signal), and by consolidation of many latent spaces (the cited prior art method uses a single one) is capable of producing latent factors which are predictive of response to targeted therapies as well as combination therapies (the cited prior art method was only shown to be predictive of response to monotherapy with cytotoxic chemotherapy).

B) Example Use Case: Latent Factors Predict Patient Survival

The use of latent factors to predict patient survival has been demonstrated in reference [2], in particular FIG. 2c, FIG. 5d and Supplementary FIG. 2) as well as in reference [1], FIG. 1d-g).

The same data from said reference [1] (i.e. 573 primary tumors and cancer cell lines from colorectal cancers) were used to demonstrate the superiority of the proposed method. The method presented in this application was trained with the survival duration of patients whose deaths were observed during the study period (discarding drop-outs), which resulted in 61 data points (out of 573) which included this supervision signal. Using the same down-stream analysis (following the inference of the latent space) as described in reference [1] to produce the c-Index of a Cox Proportional Hazards model, the proposed method of the present invention outperforms the results described in the existing literature handily:

| Method | c-Index mean (std) |
| --- | --- |
| Published in reference [1] | 0.79 (0.05) |
| Invention | 0.87 (0.02) |

This represents a statistically significant difference (P<0.001, two-tailed t-test).

Thus, it is shown that the invention is capable of using the survival time supervision signal in addition to the omics reconstruction signal (the cited prior art method uses only the omics reconstruction signal), as well as consolidation of multiple latent spaces (the cited prior art method uses a single one), to produce significantly superior results in patient survival prediction (a more than 10% improvement in the c-Index).

C) Example Use Case: Find Similar Patients in Cohort

The use of latent factors to find similar patients in a cohort has been demonstrated in three different ways in reference [1]. In the referenced paper [1], FIG. 2b demonstrates finding similar patients by clustering, with FIGS. 2d and 1d demonstrating that the patients so-defined as similar share molecular as well as functional traits. FIG. 1b in reference [1] demonstrates a third way of finding similar patients in a cohort using classification methods.

The same capability is expanded in reference [1] where similar tumor models are found for each patient, and further, tumor models which aren't similar enough to any patient in the cohort are flagged as such and removed (FIG. 4).

Again the data and down-stream analysis was used from reference [1], but obtaining the latent space as proposed in this application, to demonstrate the superiority of the proposed method.

For CMS subtype classification (cf. FIG. 1d in reference [1]), a latent space was obtained using the proposed method and the CMS label of patients as the supervision label. The same down-stream analysis as in reference [1] results in an auROC of 0.99 (vs. 0.98 for the published method).

Obtaining a latent space using the proposed method according to the present invention, and the survival signal as a supervision (as in the section "Example use case: latent factors predict patient survival" above), and the same down-stream analysis as in reference [1] (cf. FIG. 1d) achieves similar performance to the published method (log-rank P value<0.0001).

Thus it is shown that the consolidation of many latent spaces (the prior art citation uses a single one) as well as the use of the CMS-label or survival time as a supervision signal in addition to the omics reconstruction signal (the prior art citation uses only reconstruction), enable the invention to produce latent spaces which are superior to the prior art in empowering the discovery of similar patients in a cohort. This superiority comes both in terms of performance, and in the ability provided by the invention to request a patient similarity defined using different objectives (here, molecular subtypes, and survival time).

D) Example Use Case: Detect Disease Processes

The use of latent factors to detect disease processes has been demonstrated in reference [2]. In the referenced paper [2], FIG. 1 shows the case of cancer type detection; FIG. 2a shows the detection of several relevant clinical features; FIG. 2B demonstrates the detection of cancer subtypes; FIG. 3 demonstrates the detection of Microsatellite Instability (an important disease process in cancer); FIG. 4 demonstrates the detection of different causative lung cancer disease processes.

Using data from reference [1] (multi-omics measurements from 573 colorectal cancer primary tumors and cell lines), a latent space was obtained using the proposed method using the microsatellite instability status of each tumor as a supervision signal (as in FIG. 3 of reference [2]). A difference in the annotations of the different datasets from references [1] and [2] is that in the data from reference [1] on which results are presented here, microsatellite-unstable tumors are not further classified into MSI-h and MSI-l, but instead there are only two classifications: microsatellite stable (MSS) and microsatellite instability (MSI). The resulting auROC is 0.98, above the 0.93 of the method published in reference [2].

Thus, it is shown that the invention is capable of using latent space consolidation (the prior art citation uses a single latent space) as well as the supervision signal of microsatellite instability status, as well as the omics reconstruction signal (the prior art citation uses only the reconstruction signal), to produce a latent space which is superior in its ability to detect disease processes (here, a more than 5% increase in accuracy for detection of microsatellite instability).

REFERENCES

[1]: Ronen, Jonathan, Sikander Hayat, and Altuna Akalin. "Evaluation of colorectal cancer subtypes and cell lines using deep learning." Life science alliance 2.6 (2019).

[2]: Uyar, Bora, et al. "Multi-omics and deep learning provide a multifaceted view of cancer." bioRxiv (2021).

What is claimed is:

1. A method for analysis of omics data related to samples derived from a human, animal or disease model, comprising:

a) Determining a plurality of latent spaces by inputting the omics data into a plurality of omics neural networks in parallel and achieving a plurality of latent spaces each comprising a set of latent factors by performing the calculations of the plurality of omics neural networks in a data processing unit, wherein the output of the omics neural networks each provides a respective latent space;

b) Consolidating the plurality of latent spaces into one reproducible latent space, said consolidating including:

selecting latent factors which are similarly present in a minimum number of the plurality of latent spaces by comparing each latent factor of each of the latent spaces with each latent factor from each of the other latent spaces using a similarity or distance metric and selecting the latent factors which are present in at least a defined number N (N=integer number) of latent spaces within a given similarity range;

clustering the selected latent factors by grouping of latent factors which are present in at least a defined number N of the latent spaces together into clusters such that each cluster contains those latent factors from many latent spaces which are similar to each other according to said similarity or distance metric and thresholds; and calculating a respective average of the selected latent factors in a cluster for each of the clusters wherein the resulting average is a single latent factor related to a respective cluster, and wherein the set of single latent factors for the plurality of clusters form a consolidated latent space of the plurality of omics neural networks, wherein the step of consolidating is processed by a data processing unit;

wherein the consolidated latent factors include gene expressions and represent characteristics of the samples to be analyzed as biomarkers measured for the sample as a result of the consolidated latent factors, c) processing the stored consolidated latent factors forming a consolidated latent space obtained from the plurality of omics neural networks to at least one of i) detect disease processes, ii) predict drug responses, iii) predict patient survival probabilities or iv) find similar patients in a cohort.

2. The method according to claim 1, wherein classifying the obtained plurality of latent spaces by predicting at least one covariate at the output of a classifier.

3. The method according to claim 2, wherein at least one covariate comprises at least one of characteristics selected from the group of quantitative or qualitative phenotypic measurements, quantitative or qualitative cellular measurements, quantitative or compositional tissue or organ measurements, clinical patient data, historical patient data, or data related to sample processing.

4. The method according to claim 2, wherein at least one covariate comprises at least one of characteristics selected from the group of undesired batch effects, patient survival probability, drug response, undesired separation between model classes, tumor stage, relevant exposure histories, tumor microenvironment composition, T cell exhaustion, B cell exhaustion, immunomodulatory score, imaging derived features, tumor cell replication rate, tumor microbiome environment composition, probability of metastasis, tumor subtype classification, pathway activity scores, gene essentiality score, signaling pathway activation, propensity to differentiation and stemness score.

5. The method for training the plurality of omics neural networks provided for the method according to claim 2, wherein determining a plurality of latent spaces by inputting the omics data into a plurality of omics neural networks in parallel and achieving a plurality of latent spaces each comprising a set of latent factors by performing the calculations of the plurality of omics neural networks in a data processing unit, wherein the output of the omics neural networks each provides a respective latent space includes:

Predicting at least one covariate as output of a classifier by use of the obtained plurality of latent spaces; and Training of the plurality of omics neural networks by use of the error between the predicted at least one covariate and a respective known covariate related to the omics data, wherein the plurality of omics neural networks are trained to improve the posterior probability distribution of the latent spaces produced by the plurality of omics neural networks and to predict a set of predefined desired covariates by feedback of the at least one error between the predicted at least one covariate and a respective known covariate related to samples derived from a human, animal or disease model.

6. The method according to claim 1, wherein determining the omics features included in the set of omics data which affect a selected latent factor used as biomarker, wherein a matrix of the products of the absolute values of weights of at least one of the omics neural networks is determined to represent the neural path product for the interaction of each omics feature included in the set of omic data and each latent factor, and wherein the omics feature having a value of the neural path product in the matrix of products above a threshold are determined as omics features which affects the latent factor which is linked to the omics feature in the matrix by the neural path product.

7. The method according to claim 1, wherein the omics data are related to one or more quantitative or qualitative, direct or indirect, measurements of molecular constituents of a cell or of a group of cells, related to samples derived from human, animal or disease models, in particular to at least one of gene expression, number of gene copies, alterations of gene copies, mutation, methylation, proteomics, phosphoproteomics, metabolomics, microbiomics, chromatin accessibility measurement, DNA localization of proteins, DNA localization of histone posttranslational modifications, RNA modifications, DNA modifications, transcriptional rates, RNA stability, transcript expression, splicing quantification, gene fusions, DNA structural variation, RNA structural measurements, translational rates and differential polyadenylation.

8. The method according to claim 1, wherein the plurality of omics neural networks each comprising a stacked variational encoder to extract latent factors and a decoder to extract omics data from the latent factors provided as output of the related stacked variational encoder.

9. The method according to claim 1, wherein the latent factors in the latent spaces determined by the plurality of omics neural networks comprises a defined number N of selected latent factors and/or latent factors determined to be related to a characteristic of interest of the analyzed sample.

10. The method according to claim 1, wherein the consolidated latent factors are related to at least one of the samples of humans, animals or disease models related to the omics data.

11. The method according to claim 10, wherein the consolidated latent factors are related to at least one quantitative or qualitative phenotypic measurements, quantitative or qualitative cellular measurements, quantitative or compositional tissue or organ measurements, clinical patient data, historical patient data, or data related to sample processing.

12. The method according to claim 1, wherein the omics data have been extracted from at least one sample of a human, animal or disease model.

13. A non-transitory computer-readable storage medium comprising instructions which, when executed by a computer, cause the computer to carry out the steps of the method claim 1.

14. A data processing apparatus comprising a processor configured to carry out the steps of the method of claim 1.

15. The method according to claim 1, further comprising setting up a consolidated combination of a plurality of omics neural networks.

* * * * *